(12) United States Patent
Lin et al.

(10) Patent No.: US 9,782,385 B2
(45) Date of Patent: Oct. 10, 2017

(54) ARTIFICIAL TEARS SOLUTION COMBINATION

(71) Applicant: National Health Research Institutes, Miaoli County (TW)

(72) Inventors: Feng-Huei Lin, Miaoli County (TW); Hsu-Wei Fang, Miaoli County (TW); Ching-Li Tseng, Miaoli County (TW); Ya-Jung Hung, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 0 days.

(21) Appl. No.: 15/142,428

(22) Filed: Apr. 29, 2016

(65) Prior Publication Data

US 2016/0317491 A1    Nov. 3, 2016

Related U.S. Application Data

(60) Provisional application No. 62/154,891, filed on Apr. 30, 2015.

(51) Int. Cl.
| | |
|---|---|
| *A61K 31/353* | (2006.01) |
| *A61K 36/82* | (2006.01) |
| *A61K 9/00* | (2006.01) |

(52) U.S. Cl.
CPC .......... *A61K 31/353* (2013.01); *A61K 9/0048* (2013.01); *A61K 36/82* (2013.01)

(58) Field of Classification Search
CPC .................................................... A61K 31/353
USPC ......................................................... 514/456
See application file for complete search history.

(56) References Cited

U.S. PATENT DOCUMENTS

| | | | | |
|---|---|---|---|---|
| 2011/0052678 A1* | 3/2011 | Shantha | ............... | A61K 9/0048 424/450 |
| 2014/0037688 A1* | 2/2014 | Berkes | ................. | A61K 35/644 424/244.1 |

* cited by examiner

*Primary Examiner* — Yong Chu
*Assistant Examiner* — Sonya Wright
(74) *Attorney, Agent, or Firm* — Chung-Ming Shih

(57) ABSTRACT

An artificial tears solution combination is composed mainly of an anti-inflammation and anti-oxidation material, a liquid viscosity-enhancing agent, and an artificial tears solution. The artificial tears solution combination is capable keeping moisture, and meanwhile having anti-inflammation and anti-oxidation capabilities. As such, it can prolong the liquid retention on ocular surfaces, to effective reduce the repeated dosing, and shorten the schedule for the dry eye syndrome.

6 Claims, 8 Drawing Sheets
(2 of 8 Drawing Sheet(s) Filed in Color)

ARTIFICIAL TEARS SOLUTION COMBINATION

CROSS-REFERENCE TO RELAYED APPLICATIONS

This application claims priority of U.S. provision No. 62/154,891 filed Apr. 30, 2015, the entire contents of which are hereby incorporated by reference.

BACKGROUND OF THE INVENTION

Field of the Invention

The present invention relates to an artificial tears solution combination, and in particular to an artificial tear solution combination capable of keeping moisture, and at the same time having anti-inflammation and anti-oxidation capabilities, and that is used to treat moderate dry eye syndrome (DES) with ocular surface inflammation.

The Prior Arts

It is well known that, having healthy eyes and good vision to see things clearly is important for daily life. Nowadays, since most of the people keep fast-paced life styles and busy working schedules, they tend to neglect to take care of their eyes. In addition, due to various risk factors, such as staying in an air-conditioned room; watching TV, computer screen, or long-time wearing contact lenses, thus tend to leading various eye diseases, and in this respect, the dry eye syndrome is a very common eye disease in clinic nowadays.

The DES can be categorized into three stages due to its clinical symptoms: mild, moderate, and severe.

The treatment of the dry eye syndrome can be varied depending on severity of the symptoms. At present, there are three kinds of treatments as follows:

1. Mild: usually artificial tears solution is used to relieve the dryness of eyes. Sometimes, eye ointment is utilized as a treatment.

2. Moderate: In this stage, DES with inflammation on ocular surface is found. Anti-inflammatory eye ointment and artificial tears solution are used concurrently for treatment. Also, incursion surgery such as tear drops blockage operation, that can reduce loss of tear drops, is adopted to relieve eye dryness.

3. Severe: In this stage, only eyelid suture operation or saliva gland transplantation can be adapted to increase tear production for relieving the eyes from dryness.

Further, for a healthy eye under fluorescein staining, the ocular surface, especially cornea, is transparent. However, for a person having DES thus causing cornea epithelium damage, his/her eyes under fluorescein staining test tend to be blurred and spotted due to staining on the impaired cells.

Refer to Table 1 for contains of artificial tears solution presently available on the market.

TABLE 1 contains of artificial tears solution available on the market.

| Manufacturer | Contents |
|---|---|
| HYPO TEARS LUBRICATING EYE DROPS | Polyvinyl Alcohol |
| MEDICINE Hi Tears 1.4% (artificial tears solution) | Polyvinyl Alcohol |
| Dearen Artificial Tears "Wantanabe" | Potassium Chloride Sodium Chloride (eq to DISOD. Hydrogen Phosphate) (eq to Disodium Phosphate) |

TABLE 1-continued contains of artificial tears solution available on the market.

| Manufacturer | Contents |
|---|---|
| Synpac-Kingdom (artificial tears solution) | Sodium Carbonate Anhydrous Hydroxypropylmethyl Cellulose (eq to Hypromell Osehydromellose) (HPMC) |
| NEW I TEN RIN artificial tears solution | Potassium Chloride Sodium Chloride |
| NEW I TEN RIN artificial tears solution lubricant | Dextran 70 Glycerin (eq to Glycerol) |

In this respect, Epigallocatechin gallate (EGCG) is the most abundant component in the Catechin of green tea, it has been proved as having anti-inflammation and anti-oxidation effect. Therefore, it is capable of suppressing multiple inflammation factors (Megan E. Cavet, et al., Molecular Vision Biology and Genetics in Vision Research, 2011 February, 17: 533-543).

Hyaluronic acid (HA) is a natural biological substance, and is a kind of extracellular matrix. According to the research report, it plays an important role in wound healing and inflammation processing (MInoue and C Katakami, Investigative Ophthalmology & Visual Science, 1993 June, 34(7):2313-2315). Besides, it is usually utilized in treating eye dryness. The reason for this is that, H A is able to increase the viscosity of solution, to prolong the time of solution staying on the ocular surface (Papa V, Aragona P. Russo S. et al. Ophthalmologica 2001; 215:124-7, Stern M E, Beuerman R W, Fox R I, et al. Cornea 1998; 17:548-9, Mengher L S, Pandher K S, Bron A J, et al. Br J Ophthalmol 1986; 70: 422-7). In the following, refer to Table 2 for the artificial tears solution containing Hyaluronic acid (HA) as presently available on the market.

TABLE 2 the artificial tears solution containing Hyaluronic acid (HA) supplement on the market.

| Artificial tears solution having HA as available on market | contents |
|---|---|
| CIBA contact lens relief solution | Sodium Chloride Sodium Perborate Hyaluronate Sodium (eq to Sodium Hyaluronate) Sodium Phosphate Dibasic Anhydrous (eq to Disodium Hydrogen Phosphate Anhydrous) (eq to Dibasic Sodium Phosphate Anhydrous) (Disodium Phosphate Anhydrous) Sodium Phosphate Monobasic Monohydrate (Sodium Dihydrogen Phosphate Monohydrate) Dequest 2060 |
| "Kingdom" contact lens relief solution | Sodium Chloride Sodium Perborate Hyaluronate Sodium (eq to Sodium Hyaluronate) Sodium Phosphate Dibasic (eq to DISOD. Hydrogen Phosphate) (eq to Disodium phosphate) Sodium Phosphate Monobasic Monohydrate (Sodium Dihydrogen Phosphate Monohydrate) Water Distilled (eq to Distilled Water) Dequest 2060 |
| VISMED contact lens relief solution | Sodium Citrate (Sodium Citrate Tribasic) Calcium Chloride Dihydrate Magnesium Chloride Hexahydrate (eq to Magnesium Chloride 6H2O) Potassium Chloride |

TABLE 2-continued the artificial tears solution containing
Hyaluronic acid (HA) supplement on the market.

| Artificial tears solution having HA as available on market | contents |
|---|---|
| | Sodium Chloride |
| | Hyaluronate Sodium |
| | (eq to Sodium Hyaluronate) |
| | Sodium Phosphate Dibasic Dodecahydrate |
| | (eq to Disodium phosphate Dodecahydrate) |
| | Wather for Injection |

However, as shown in Tables 1 and 2, for the contains of the artificial tears solutions presently available on the market, most of them are buffer solution of salts without adding recipe for treating inflammation, such that its function is restricted only to provide moisture for relieving dryness of eyes. Moreover, a part of artificial tears solutions presently available on the market contains preservatives, thus leading to worsen the dry eye syndrome (Ankita S. Bhaysar, et al., Oman J Ophthalmol. 2011 May-August; 4(2):50-56).

Presently, for the treatment of moderate eye dryness syndrome, ophthalmologists often prescribe eye ointment, liquid medicine (eye drop), artificial tears solution or anti-inflammation agents for treat DES separately, and usually use multi-agents in order. However, due to the busy life style, people has no patience for take multi-agents and usually only take one agent and forget to take other agents, thus leading to effective-less therapy and prolonging treatment period. In addition, the applying of ointment could cause blurring of vision of patients, hereby resulting in inconvenience of patient's activity.

Further, after being dipped onto the ocular surface for about 5 minutes, the artificial tears solution or liquid agents (eye drops) tend to not remain on the ocular surface, due to evaporation or the nasolacrimal duct drainage, thus causing poor ocular drug bioavailability. For this reason, in prescribing eye drops, ophthalmologists usually advise patients to apply it 3 to 4 times per day, and after applying one eye drop for 5 minutes, then can dipping another one. However, for a patient who suffered multi-agents therapy, he/she needs separately and repeatedly dropping many lead to inconvenience to the patient, thus adversely affecting the therapeutic outcome.

Therefore, presently, the preparation and performance of artificial tears solution is not quite satisfactory, and it has some methods to improve the therapeutic effect of artificial tear solution for DES treatment.

SUMMARY OF THE INVENTION

In view of the problems and drawbacks of the prior art, the present invention provides an artificial tears solution combination capable of keeping moisture, and at the same time having anti-inflammation and anti-oxidation capabilities, to reduce the repeated dosing problem, to overcome the drawback of the Prior Art.

A major objective of the present invention is to provide an artificial tears solution combination capable of keeping moisture, and at the same time having anti-inflammation and anti-oxidation capabilities, to treat the moderate eye dryness syndrome with ocular surface inflammation.

In order to achieve the objective mentioned above, the present invention provides an artificial tears solution combination capable of keeping moisture, and at the same time having anti-inflammation and anti-oxidation capabilities, including: an anti-inflammation and anti-oxidation material, such as Epigallocatechin gallate (EGCG); and a viscosity enhancing agent, such as Hyaluronic acid (HA); and an artificial tears solution.

Another objective of the present invention is to provide an artificial tears solution combination capable of prolonging its retention on the ocular surface and providing anti-inflammation effect at the same time, to effectively reduce repeated dosings and shorten the treating process for the moderate DES with ocular surface inflammation.

In order to achieve the objective mentioned above, the present invention provides an artificial tears solution compound, that is realized by adding a viscosity enhancing agent, for example Hyaluronic acid (HA), into an artificial tears solution, to prolong the retention of artificial tears solution on the ocular surface, in achieving anti-inflammation effect at the same time, thus effectively shortening repeated dosing processes for treating moderate DES with ocular surface inflammation.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from the detailed descriptions.

BRIEF DESCRIPTION OF THE DRAWINGS

The application file contains at least one drawing executed in color. Copies of this patent or patent application publication with color drawing(s) will be provided by the Office upon request and payment of the necessary fee. The related drawings in connection with the detailed descriptions of the present invention to be made later are described briefly as follows, in which.

DETAILED DESCRIPTION OF THE PREFERRED EMBODIMENT

The purpose, construction, features, functions and advantages of the present invention can be appreciated and understood more thoroughly through the following detailed description with reference to the attached drawings.

Embodiment 1

The present invention provides an artificial tears solution combination, composed of a material having anti-inflammation and anti-oxidation capabilities, and a material having liquid viscosity enhancing capability, The compound is used in an experiment to study whether it could adversely affect the activity of Human Corneal Epithelial Cells (HCEC), or it's harmful to Human Corneal Epithelial Cells (HCEC), and whether it can inhibit inflammation of Human Corneal Epithelial Cells (HCEC).

In the present embodiment, the material having anti-inflammation and anti-oxidation capabilities is Epigallocatechin gallate (EGCG); while the material as viscosity enhancing agent is Hyaluronic acid (HA).

The concentration of Epigallocatechin gallate (EGCG) utilized is in a range from 1 µg/ml to 200 µg/ml; while the weight/volume percent (wt./v %) for Hyaluronic acid (HA) is in a range from 0.01% to 0.3%.

Cellar Activity Experiment

In this experiment, firstly cultivate the Human Corneal Epithelial Cells (HCEC) for 24 hours, then utilize Lipopolysaccharide (LPS) at concentration of 500 ng/ml to induce HCEC for 3 hours, to make it to produce inflammation reaction. Afterwards, add in the compound of EGCG and HA to cultivate it for 3 days. The cellar activity experiment is proceeded for 5 days, and the results of the experiment are obtained by collecting the cells on the first day and the third day. The prior art WST-8 is used in cooperation with Enzyme-Linked Immunosorbent Assay (ELISA) plate reader, to measure the relative light absorption for wavelengths 450 nm, to detect cell activity.

Figure 1A:
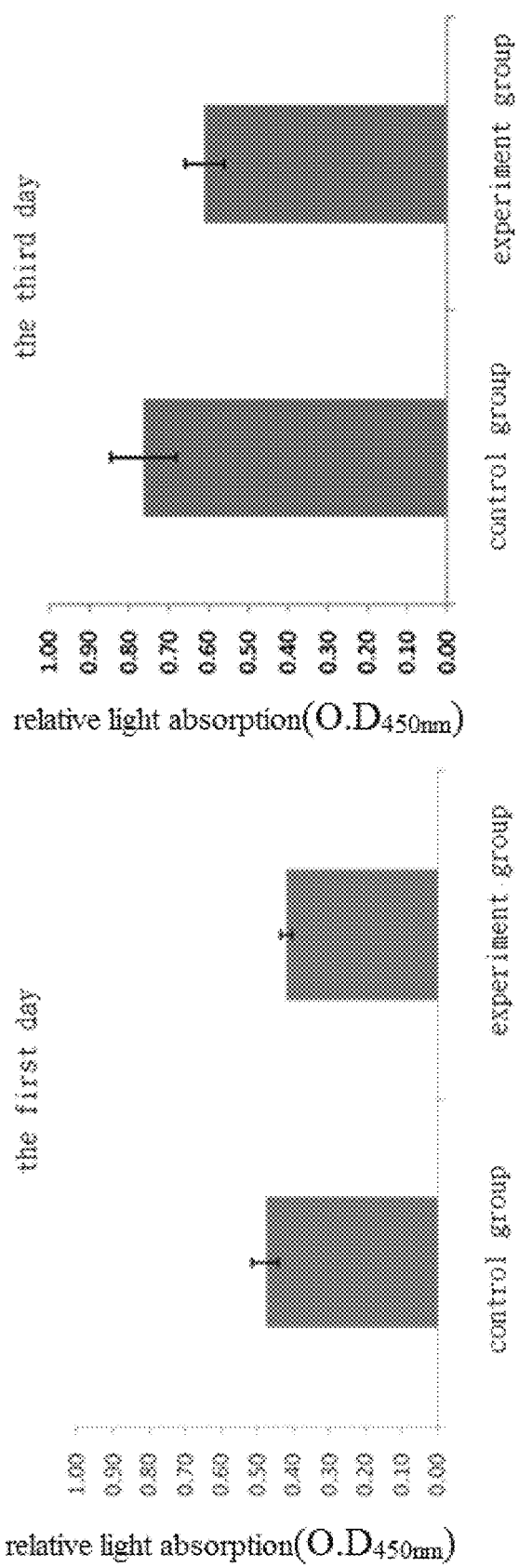
FIG. 1A is a diagram showing the effect on the cell activity by an artificial tears solution combination of the present invention.

The results of the experiment are shown in FIG. 1A. As shown in FIG. 1A, the control group is the normal Human Corneal Epithelial Cells (HCEC) (without Lipopolysaccharide (LPS) addition for induce inflammation). While the experimental group indicates the effect on the cell activity by adding compound of EGCG and HA. Again, as shown in FIG. 1A, for the first day, the relative light absorptions of the experimental group and the control group show no statistically significant differences. In addition, for the third day, the relative light absorptions of the experimental group and the control group also show no statistically significant differences. Therefore, the conclusion is that, the compound of EGCG and HA does not have adverse effect on the cellar activity.

Cellar Toxicity Experiment

In this experiment, firstly cultivate the Human Corneal Epithelial Cells (HCEC) for 24 hours, then utilize Lipopolysaccharide (LPS) at concentration of 500 ng/ml to induce HCEC for 3 hours, to make it to produce inflammation reaction. Afterwards, add in the compound of EGCG and HA to cultivate it for 3 days. The cellar toxicity experiment is proceeded for 5 days, and the results of the experiment are obtained by collecting the cells on the first day and on the third day. The prior art LDH is used in cooperation with Enzyme-Linked Immunosorbent Assay (ELISA) plate reader, to measure the relative light absorption for wavelengths 490 nm, to detect cell toxicity.

Figure 1B:
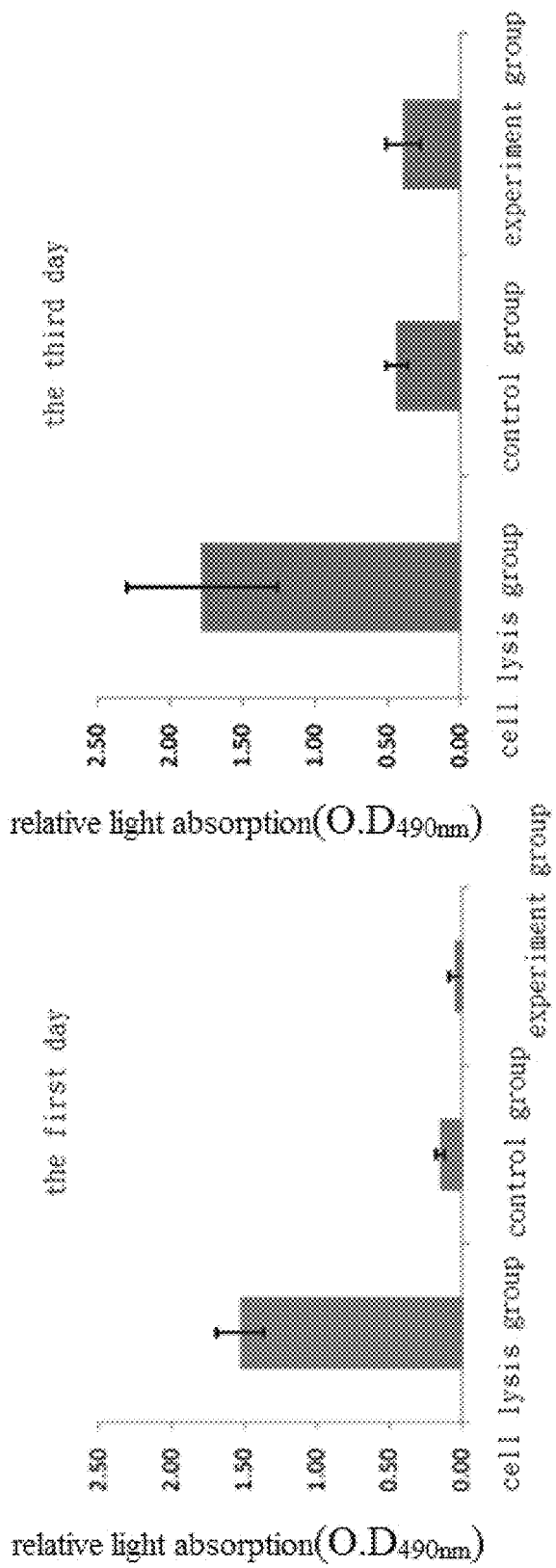
FIG. 1B is a diagram showing the effect on the cell toxicity by an artificial tears solution combination of the present invention.

The results of the experiment are shown in FIG. 1B. As shown in FIG. 1B, the cell lysis group is a negative control group. The control group is the Human Corneal Epithelial Cells (HCEC) (without Lipopolysaccharide (LPS) addition for induce inflammation). The experimental group is HCEC cultured with added compounds of EGCG and HA. Again, as shown in FIG. 1B, for the first day, the relative light absorptions of the experimental group and the control group show no statistically significant differences; for the third day, the relative light absorptions of the experiment group and the control group also show no statistically significant differences. Therefore, the conclusion is that, the compounds of EGCG and HA in the present invention does not harmful to the HCEC cells.

Gene Expression Experiment for Inflammatory Cytokines Evaluation

In this experiment, firstly, cultivate the Human Corneal Epithelial Cells (HCEC) for 48 hours, then utilize Lipopolysaccharide (LPS) at concentration of 500 ng/ml to induce HCEC for 3 hours, to make it to produce inflammatory reaction. Afterwards, add in the compound of EGCG and HA to cultivate with HCEC for 2 hours. The Gene Expression Experiment to evaluate Inflammatory cytokines was conducted for 3 days, and the samples for this experiment were obtained by collecting these cells on the third day. Firstly, utilize Trizol reagent to extract Ribonucleic Acid (RNA) of these cells, and then utilize the High-Capacity cDNA Reverse Transcription Kits made by manufacturer ABi to perform Reverse Transcription Polymerization reaction (RT-PCR), to synthesis the complementary deoxyribonucleic acid (cDNA). Subsequently, utilize the TagManR Fast Universal Master Mix (2X) made by manufacturer ABi, to perform Quantitative Real-Time PCR (Q-PCR) on the inflammatory cytokines (IL-1$\beta$, IL-6, IL-8, and TNF-$\alpha$), to detect the gene expression of the inflammation cytokines (IL-1$\beta$, IL-6, IL-8, and TNF-$\alpha$).

Figure 2:
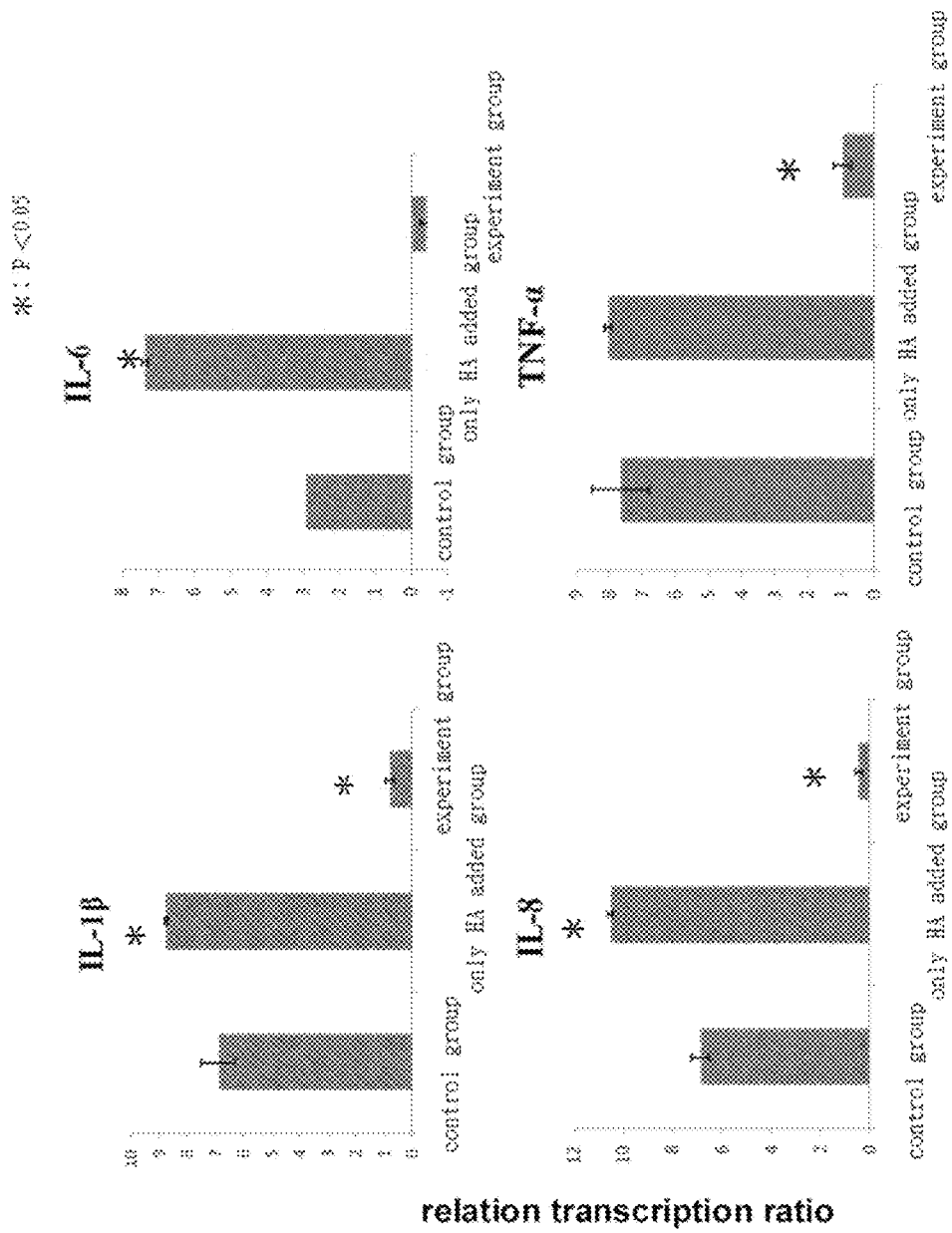
FIG. 2 is a diagram showing the effect on the inflammation factor by an artificial tears solution combination of the present invention.

The results of the experiment are as shown in FIG. 2, for the control group, the Human Corneal Epithelial Cells (HCEC) not being induced by Lipopolysaccharide (LPS) to produce inflammatory reaction; for the only HA added group, only HA is added; and for the experimental group, the compound of EGCG and HA is added. As shown in FIG. 2, in the experimental group, the Relative Transcription Ratios of the 4 inflammation factors are lower than the other two groups, that indicates that the gene expression of the inflammatory cytokines is reduced. In the only HA added group, the Relative Transcription Ratios of the 4 inflammation cytokines are higher than the other two groups, that indicates that HA has no effect on the reduction of the inflammatory cytokines. Therefore, it is confirmed that, EGCG does have anti-inflammatory effect on the human corneal epithelium cells.

In the present embodiment, the WST-8, LDH, RT-PCR, and Q-PCR belong to the prior art. Further, the technology of using Trizol reagent to extract RNA of cells also belong to the prior art. Therefore, they are not going to repeat here for brevity.

Experiment 2

The experiment is used to determine whether the physiological characteristics, such as the pH value, the osmolarity, and viscosity of human tear, and that of the combination of EGCG and HA are similar.

In implementing the experiment, the following devices are utilized: a pH meter, for example, pH meter of model pH 510 made by manufacturer EUTECH INSTRUMENTS; a micro-osmotic pressure machine, for example, micro-osmotic pressure machine of model 3320 made by manufacturer Advanced Instrument; a programmable Rheometer (detecting viscosity), for example, a computer programmable Rheometer of model DVIII, made by manufacturer Brookfield.

These results of the experiment are shown in Table 3. As shown in Table 3, the physiological characteristics of the combination of EGCG and HA are very similar to that of normal human tear.

TABLE 3 comparison of characteristics between normal human tear and EGCG & HA combination

| | pH value | osmotic pressure (mOsm/kg) | viscosity (mpas) |
|---|---|---|---|
| characteristic of normal human tear | 6.2-9 | 260-340 | 9 |
| characteristic of EGCG and HA combination | 7-8.5 | 255-280 | 6.5-7.5 |

In the present embodiment, the pH meter, the microosmolarity machine and the micro computer programmable Rheometer all belong to the prior art, thus they will not be repeated here for brevity.

Embodiment 3

The present embodiment provides an artificial tear solution combination, composed of a material having anti-inflammation and anti-oxidation capabilities, a material as viscosity enhancing agent, and an artificial tear solution. The artificial tear solution compound is used to conduct effectiveness test experiment for treating dry eye syndrome.

In this experiment, the material having anti-inflammation and anti-oxidation capabilities is EGCG while the material as viscosity enhancing agent is HA.

The concentration of EGCG utilized is between 1 μg/ml and 200 μg/ml; while the concentration of HA is that of the HA contained in the artificial tear solution presently available on the market, with its weight percentage between 0.01% to 0.3%. In the present embodiment, the artificial tears solution does not contain HA and preservative, such that it is composed of sodium chloride, potassium chloride, calcium chloride, and sodium di-hydrogen phosphate.

Tear Production Test (Schirmer Test)

In this experiment, firstly, a Benzalkonium Chloride (BAC) is dipped onto the eyes of an animal (for example the New Zealand white rabbits) 3 times a day for 3 weeks, to induce rabbits eyes to mimic moderate dry eye syndrome with inflammatory symptoms. Then, utilize various combined compounds of artificial tear solution, HA, and EGCG to proceed with treatment, twice a day for 2 weeks.

The Schirmer Test is a Tear Production Test, and is used to measure tear amount of a patient having dry eye syndrome in clinic. Wherein, a test paper is placed at the lower eyelid, then observe tear amount through caterpillar phenomenon as wetted length (in unit mm).

Figure 3:
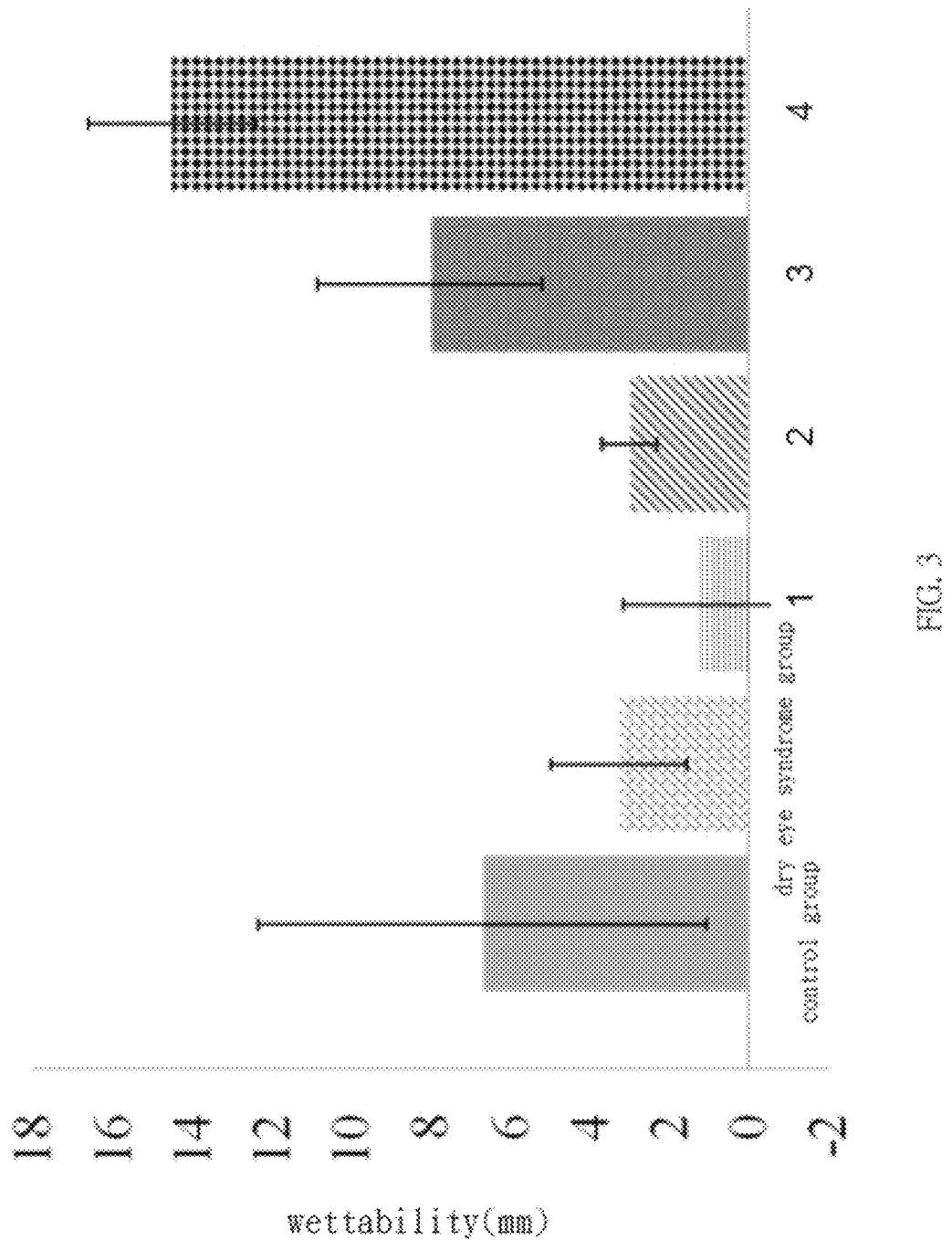
FIG. 3 is a diagram showing the results of Schirmer test after an animal having moderate eye dryness syndrome is treated with an artificial tears solution combination of the present invention.

The result of this experiment is as shown in FIG. 3, for the variant treatment groups as follows: a control group, that does not have dry eye syndrome; a dry eye syndrome group, the dry eye syndrome is a moderate eye dryness syndrome induced through using BAC; group 1, an artificial tear solution treatment; group 2, an artificial tear solution plus HA treatment; group 3, an artificial tear solution plus EGCG treatment; and group 4, artificial tear solution combination treatment. As shown in FIG. 3, through the treatment of the artificial tear solution combination, for the group 4, the artificial tear solution combination treatment, its tear amount restored to mimic normal value.

Inflammation Cytokines-Protein Expression Experiment

Figure 4:
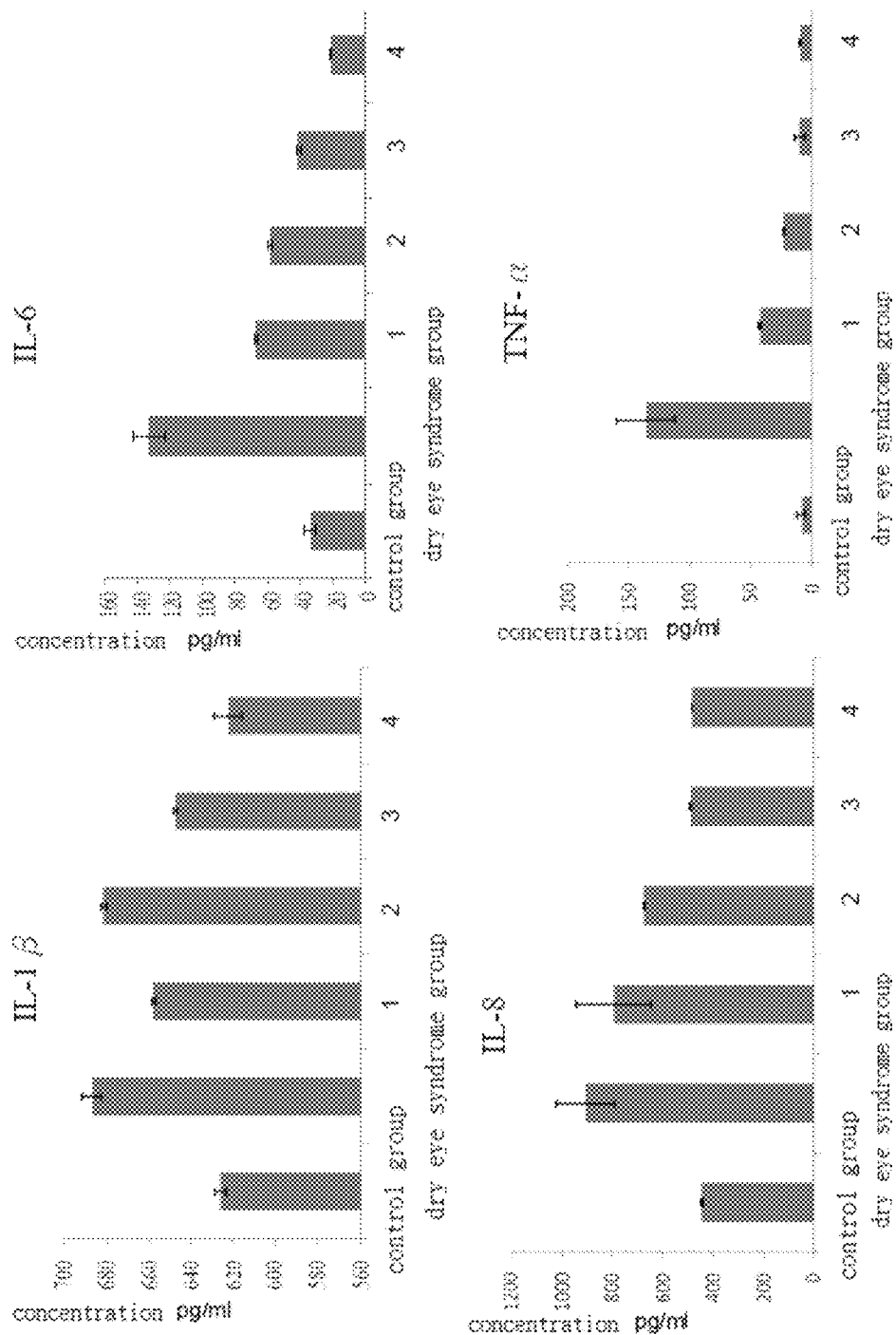
FIG. 4 is a diagram showing the variations of inflammation factors after an animal having moderate eye dryness is treated with an artificial tears solution combination of the present invention.

In this experiment, firstly, a Benzalkonium Chloride (BAC) is dipped onto the eyes of a rabbit 3 times a day for 3 weeks, to induce the rabbit eyes to produce inflammation, and to cause it to have symptoms of moderate dry eye syndrome. Then, utilize various combined compounds of artificial tear solution, HA, and EGCG to proceed with treatments, twice a day for 2 weeks. Then, extract the protein from the rabbit's cornea to perform Enzyme-Linked Immunosorbent Assay (ELISA), to detect the protein expression of the inflammation cytokines (IL-1β, IL-6, IL-8, and TNF-α), and to observe and determine whether the inflammation cytokines were reduced, through treatment of various compounds of artificial tear solution, HA, and EGCG The result of this experiment is shown as FIG. 4, for the variant treatment groups as follows: a control group, that does not have induced dry eye syndrome; a dry eye syndrome group, the dry eye syndrome is a moderate eye dryness syndrome induced through using BAC; group 1, an artificial tear solution treatment; group 2, an artificial tear solution plus HA treatment; group 3, an artificial tear solution plus EGCG treatment; and group 4, artificial tear solution combination treatment. As shown in FIG. 4, group 3, the artificial tear solution plus EGCG treatment, and group 4, the artificial tear solution combination treatment, the concentration of variant inflammatory cytokines (IL-1β, IL-6, IL-8, and TNF-α) are significantly decreased, with their concentration finally similar to the control group. While, in the artificial tear solution treatment group 1 and the artificial tear solution plus HA treatment group 2, after treatment, inflammatory cytokines (IL-1β, IL-6, IL-8, and TNF-α) do not show significant reduce, and that means EGCG has the anti-inflammatory effect confirmed by the result of the reduction of inflammatory cytokines (IL-1β, IL-6, IL-8, and TNF-α).

Eye Ball Fluorescein Staining Examination

In this experiment, firstly, a Benzalkonium Chloride (BAC) is dipped onto the eyes of New Zealand white rabbits 3 times a day for 3 weeks, to induce the rabbit eyes to inflammation, to cause it to have symptoms of moderate dry eye syndrome. Then, utilize the artificial tear solution combination to treat the inflammatory eyes twice a day for two weeks. Subsequent, perform Fluorescein Staining Examination for the eyes of rabbit.

Figure 5:
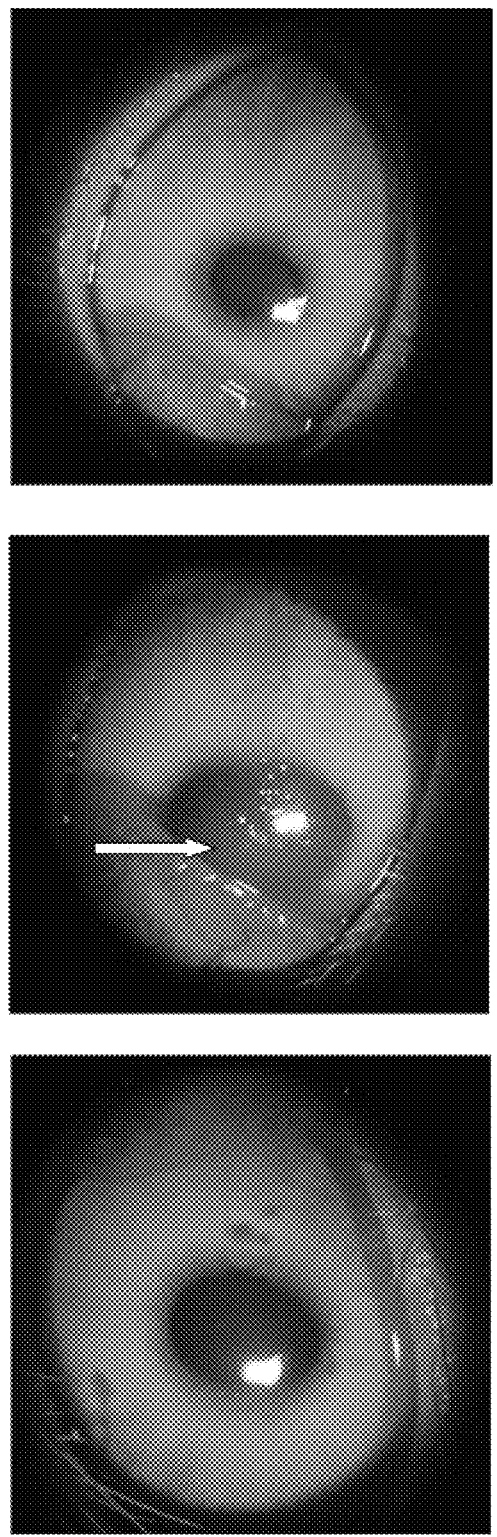
FIG. 5 is a diagram showing the results of ocular surface fluorescein staining after an animal having moderate eye dryness syndrome is treated with an artificial tears solution combination of the present invention.

The result of the experiment is shown as in FIG. 5, for the variant treatment groups as follows: a control group, that does not have dry eye syndrome; a dry eye syndrome group, the dry eye syndrome is a moderate eye dryness syndrome induced through using BAC; and a treatment group, that utilizes the artificial tear solution combination (group 4) for treatment. As shown in FIG. 5, in the treatment group utilizing the artificial tear solution combination, after treatment, the eyes return to transparent, without blurring or stain spots.

Histological Examination of Cornea Tissue

In this experiment, firstly, a Benzalkonium Chloride (BAC) is dipped into the eyes of New Zealand white rabbits 3 times a day for 3 weeks, to induce the rabbit eyes to get inflammation, and to cause it to have symptoms of moderate dry eye syndrome. Then, utilize the artificial tear solution combination to treat the inflammatory eyes twice a day for two weeks. Subsequently, perform histological section of cornea from tested rabbits, then staining it with hematoxylin and eosin stain (namely, HE stain), and then examined section by a microscope under 10-fold object lens to observe the corneal section.

Figure 6:
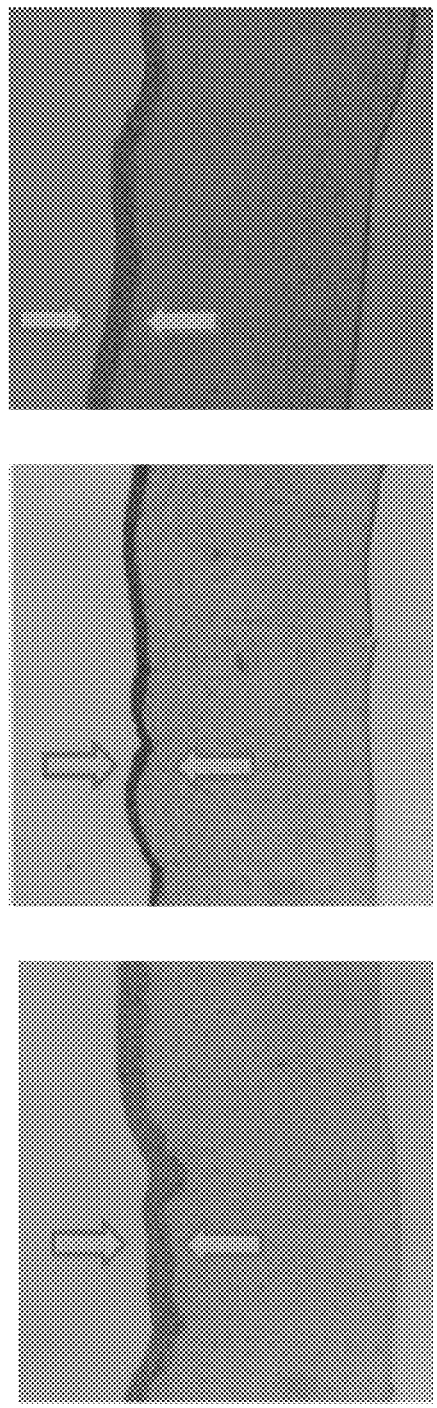
FIG. 6 is a diagram showing the variations of Corneal Epithelial Cells and Corneal thickness after an animal having moderate dry eye syndrome is treated with an artificial tears solution combination of the present invention.

For New Zealand white rabbits having moderate dry eye syndrome with inflammation, the thickness of the cornea becomes thinner (originally 3 to 5 layers of epithelial cell reduced to 1 to 3 layers), and the overall thickness of cornea was also reduced. This phenomenon is as shown in FIG. 6, wherein it shows a control group that does not have dry eye syndrome; a dry eye syndrome group, that has a moderate eye dryness syndrome induced through using BAC; and a treatment group, that utilizes the artificial tear solution combination of the present invention for treatment. Again, as shown in FIG. 6, for the treatment group utilizing the artificial tear solution combination of the present invention, after treatment, the layered cornea epithelium cells arrangement was restored to its normal structure in the tested rabbits, and the overall thickness of cornea is returned to mimic normal eye.

Ocular Surface Retention Test for the Artificial Tear Solution Combination

In this experiment, dipping the artificial tear solution with fluorescence supplement having only added EGCG and the artificial tear solution combination of the present invention into the eyes of two individual animals (for example, mice), and after 15 minutes, utilize a non-invasion 3D Molecular Imaging System (IVIS Spectrum System) made by manufacturer Xenoge, to observe the retention time of the fluorescent artificial tear solution on the ocular surfaces of the mice via fluorescence observation.

Figure 7:
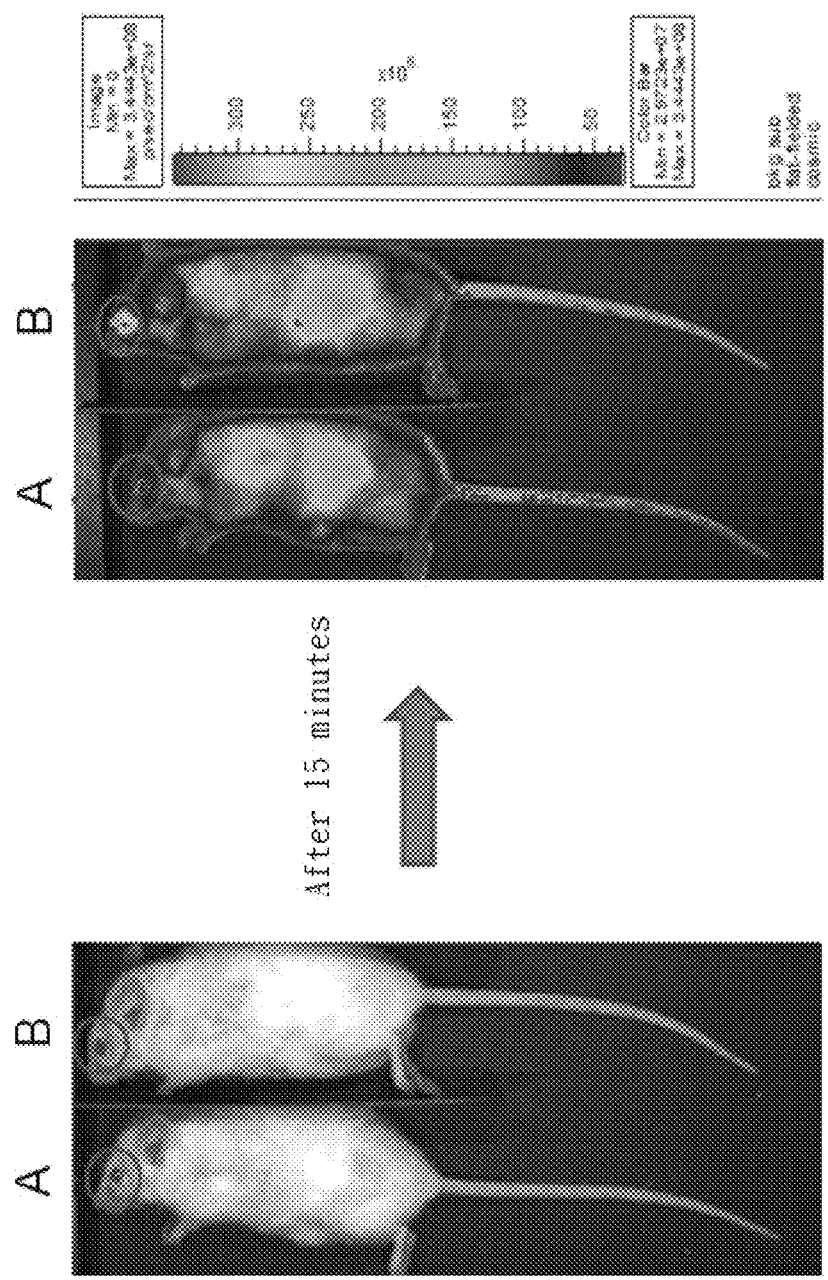
FIG. 7 is a diagram in colors showing the comparisons of ocular surface retention after an animal being treated with an artificial tears solution combination added with Hyaluronic acid (HA) of the present invention.

The experiment result is as shown in FIG. 7, wherein, it shows an artificial tear solution plus only EGCG group A, and an artificial tear solution combination (containing HA and EGCG) group B. As shown in FIG. 7, for artificial tear solution combination (containing HA and EGCG) group B, the solution will remain on the ocular surface after it being dipped for 15 minutes; while for artificial tear solution plus only EGCG group A, the solution does not remain on the ocular surface after it being dipped for 15 minutes. Therefore, for the group B having added HA, it can increase the liquid (namely, the artificial tear solution combination of the present invention) viscosity, to prolong the liquid retention on the ocular surface, to effectively reduce the repeated dosings frequency, and then shorten the treatment process for the moderate dry eye syndrome.

In the present embodiment, for the Schirmer Test, ELISA, Eye Ball Fluorescein Staining, hematoxylin and eosin staining utilized, they all belong to the Prior Art. Besides, IVIS Spectrum System is the instrument of the prior art. Thus, they are not going to repeat here for brevity.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements, which are within the scope of the appended claims.

What is claimed is:

1. An artificial tears solution combination, comprising: an anti-inflammation and anti-oxidation material, a viscosity-enhancing agent, and an artificial tears solution, wherein said artificial tears solution includes sodium chloride, potassium chloride, calcium chloride, and sodium di-hydrogen phosphate.

2. The artificial tears solution combination as claimed in claim 1, wherein said anti-inflammation and anti-oxidation material is Epigallocatechin gallate (EGCG).

3. The artificial tears solution combination as claimed in claim 1, wherein said viscosity-enhancing agent is Hyaluronic acid (HA).

4. The artificial tears solution combination as claimed in claim 2, wherein concentration of Epigallocatechin gallate (EGCG) is 1 µg/ml to 200 µg/ml.

5. The artificial tears solution combination as claimed in claim 2, wherein said Epigallocatechin gallate (EGCG) is Catechin of green tea.

6. The artificial tears solution combination as claimed in claim 3, wherein weight/volume percent of Hyaluronic acid (HA) is 0.01% to 0.3%.

* * * * *